US012144646B2

(12) United States Patent
Hao et al.

(10) Patent No.: US 12,144,646 B2
(45) Date of Patent: Nov. 19, 2024

(54) ASSEMBLED, DOWNWARD-PRESSING, MULTIFUNCTIONAL EEG CAP

(71) Applicants: Xuanwu Hospital Capital Medical University, Beijing (CN); Beijing Municipal Geriatric Medical Research Center, Beijing (CN)

(72) Inventors: Junwei Hao, Beijing (CN); Haijie Liu, Beijing (CN); Penghu Wei, Beijing (CN); Xiyue Zhang, Beijing (CN); Teng Chen, Beijing (CN)

(73) Assignees: Xuanwu Hospital Capital Medical University, Beijing (CN); Beijing Municipal Geriatric Medical Research Center, Beijing (CN)

( * ) Notice: Subject to any disclaimer, the term of this patent is extended or adjusted under 35 U.S.C. 154(b) by 783 days.

(21) Appl. No.: 17/303,639

(22) Filed: Jun. 3, 2021

(65) Prior Publication Data
US 2022/0151555 A1    May 19, 2022

(30) Foreign Application Priority Data

Nov. 19, 2020   (CN) .......................... 202011307603.8
Mar. 5, 2021    (CN) .......................... 202110249014.7

(51) Int. Cl.
*A61B 5/00*    (2006.01)
*A61B 5/251*   (2021.01)
(Continued)

(52) U.S. Cl.
CPC ............ *A61B 5/6803* (2013.01); *A61B 5/251* (2021.01); *A61B 5/274* (2021.01); *A61B 5/291* (2021.01)

(58) Field of Classification Search
CPC ...................... A61B 5/6803; A61B 5/291–388
See application file for complete search history.

(56) References Cited

U.S. PATENT DOCUMENTS 9,622,702 B2 * 4/2017 Badower ................ A61B 5/291
2009/0171788 A1 * 7/2009 Tropper ................ A63F 13/212
705/14.61
(Continued)

FOREIGN PATENT DOCUMENTS

CN    202821347 U    3/2013
CN    203914913 U    11/2014
(Continued)

*Primary Examiner* — Etsub D Berhanu
(74) *Attorney, Agent, or Firm* — Ping Wang; Kalos Athena Wang PLLC (57) ABSTRACT

The present invention relates to an assembled, downward-pressing, multifunctional electroencephalogram (EEG) cap, at least comprising: a cap body, configured to be worn on a head of a patient, and formed by a plurality of constituent blocks, wherein each of the constituent blocks comprises a first unit and a second unit that carry extracranial electrodes for detecting EEG signals from corresponding areas of the head of the patient, in which the first unit and the second unit are configured to perform relative movements and thereby change their relative positions, the first unit and the second unit being shaped to fit a curved surface of the head of the patient; the first unit of the constituent block being movably connected to the second unit by means of a drive system provided between at least a part of the first unit and a part of the second unit, wherein the extracranial electrodes located on the first unit and on the second unit are configured to at least follow the relative movements between the first unit and the second unit in a first direction so as to move toward and/or away from an EEG measuring area on the head of the patient.

13 Claims, 4 Drawing Sheets

(51) Int. Cl.
    *A61B 5/274*     (2021.01)
    *A61B 5/291*     (2021.01)
    *A61B 5/369*     (2021.01)

(56)           References Cited

U.S. PATENT DOCUMENTS

| | | | |
|---|---|---|---|
| 2013/0237146 A1* | 9/2013 | Serota | G02B 27/017 455/12.1 |
| 2014/0350431 A1* | 11/2014 | Hagedorn | A61B 5/4836 600/15 |
| 2015/0374971 A1* | 12/2015 | Dar | A61B 5/291 607/139 |
| 2017/0215753 A1* | 8/2017 | Lee | A61B 5/6803 |
| 2018/0153470 A1 | 6/2018 | Gunasekar et al. | |
| 2021/0023368 A1 | 1/2021 | Shakour et al. | |
| 2021/0259635 A1* | 8/2021 | Remes | A61B 5/291 |

FOREIGN PATENT DOCUMENTS

| | | | |
|---|---|---|---|
| CN | 207707910 U | 8/2018 | |
| CN | 109464143 A | 3/2019 | |
| CN | 209122229 U | 7/2019 | |
| CN | 212066710 U | 12/2020 | |
| WO | WO-2019088607 A1 * | 5/2019 | A61C 19/04 |

\* cited by examiner

ASSEMBLED, DOWNWARD-PRESSING, MULTIFUNCTIONAL EEG CAP

CROSS-REFERENCE TO RELATED APPLICATIONS

This application claims the benefit of the Chinese Patent Applications No. CN202011307603.8 filed on Nov. 19, 2020 and No. CN202110249014.7 filed on Mar. 5, 2021, which are hereby incorporated by reference as if fully set forth herein.

BACKGROUND OF THE INVENTION

1. Technical Field

The present invention relates to electroencephalogram (EEG) examination, and more particularly to an assembled, downward-pressing, multifunctional EEG cap.

2. Description of Related Art

EEG refers to a technology for collecting a sum of brain bioelectrical signals at the scalp surface. It serves to record changes in brainwaves, represents a sum of changes in potentials of nerve cells, and provides an overall reflection of changes in cerebral neurons at the cerebral cortex or brain surface. EGG waves are spontaneous, rhythmic and random. Therein, being spontaneous means that electroencephalogram exists all the time, with an amplitude of 5-200 uV, and being rhythmic means that electroencephalogram exists in a certain wave range, while being random means that electroencephalogram is irregular, with the amplitude being positive or negative randomly. Collecting electroencephalogram from different areas of the brain provides more information. An EEG wave may be $\delta$, $\theta$, $\alpha$, $\beta$, or $\gamma$, depending on its frequency. There are also waveforms like $\sigma$, $\lambda$, $\kappa$-composite waves, and $\mu$ can appear during sleep. Electroencephalogram is of clinical significance for diagnosis of epilepsy, sleep monitoring, and intensive care, and has been extensively used in scientific researches. It is also essential for cognitive neuroscience, sensory neuroscience, applied psychology, brain-computer interface, super scanning, and multi-modal simultaneous scanning. With the development of brain-computer interface technologies, EEG caps have become an important tool for signal collection. Currently, EEG caps used for the purpose of brain-computer interface are mainly saline-type caps and gel-type caps. Therein, a gel-type cap has a lower impedance and longer lasting time for its use of conductive gel.

China Patent Application Publication No. CN109464143A discloses an EEG cap, which has a plurality of extracranial electrodes magnetically attached to the inner wall of an iron housing by means of electromagnets, and has a jaw belt can automatically wind up so as to make the extracranial electrodes stay tightly on the scalp. This design, however, significantly increases the weight of the EEG cap and adds burden to the cervical vertebra of the user, making use of the cap an uncomfortable experience and therefore having negative effects on electroencephalogram tests. In addition, the strong electromagnetic field generated around the brain by the electromagnets can degrade the accuracy of electroencephalogram measurement. Besides, the automatically winding-up jaw belt uses a single power source to pull the extracranial electrodes toward the scalp of the patient, and this not only fails to ensure that all the extracranial electrodes well contact the scalp but also discomforts the patient.

China Patent Application Publication No. CN212066710U discloses a hair-entering type electroencephalogram cap, which comprises a cap body base, electroencephalogram dry electrodes and plural support rods. The support rod has its one end connected to the base and has its opposite end connected to the electroencephalogram dry electrode. The support rods are all in a bent shape and tend to gather towards the center at the other ends of the support rods. This known EEG cap have electroencephalogram dry electrodes and slender, elastic support rods. In use, the cap slides on the head of the patient to push hairs aside and let the dry electrodes contact the scalp, thereby improving accuracy of EEG signal collection.

Even though, the existing EEG caps still have many problems:

1. In order to ensure good quality of the collected data, an EEG cap has to stay tightly on the scalp, and, due to individual differences, this is difficult to achieve without an additional contract force that may, nevertheless, make the patient feel hurt.

2. Where the user has intensive, thick hairs that may hinder the extracranial electrodes from collecting EEG signals, for ensuring good contact with the scalp, the hairs usually have to be removed.

3. During collection of EEG signals, resistance generated due to the nature of the electrodes or other factors can degrade accuracy of the collected EEG signals.

To sum up, there is a need for a novel EEG cap for clinical use. The novel EEG cap preferably have at least one of the following features: allowing regional adjustment, sensing pressure-and/or resistance, and eliminating physical interference, thereby solving problems of the existing EEG measuring devices.

Since there is certainly discrepancy between the prior art comprehended by the applicant of this patent application and that known by the patent examiners and since there are many details and disclosures disclosed in literatures and patent documents that have been referred by the applicant during creation of the present invention not exhaustively recited here, it is to be noted that the present invention shall actually include technical features of all of these prior-art works, and the applicant reserves the right to supplement the application with the related art more existing technical features as support according to relevant regulations.

SUMMARY OF THE INVENTION

In view of the shortcomings of the prior art, the present invention provides an assembled, downward-pressing, multifunctional electroencephalogram (EEG) cap, at least comprising: a cap body, configured to be worn on a head of a patient, and formed by a plurality of constituent blocks, wherein each of the constituent blocks comprises a first unit and a second unit that carry extracranial electrodes for detecting EEG signals from corresponding areas of the head of the patient, in which the first unit and the second unit are configured to perform relative movements and thereby change their relative positions, and the first unit and the second unit being shaped to fit a curved surface of the head of the patient; the first unit of the constituent block being movably connected to the second unit by means of a drive system provided between at least a part of the first unit and a part of the second unit, wherein the extracranial electrodes located on the first unit and on the second unit are configured to at least follow the relative movements between the first unit and the second unit in a first direction so as to move toward and/or away from an EEG measuring area on the head of the patient.

Preferably, the constituent blocks with snap-in connectors are movably connected with adjacent constituent blocks also provided with snap-in connectors by their respective snap-in connectors, so as to form the cap body and so that when the cap body is put on the head of the patient, a distance between the adjacent constituent blocks is able to increase or decrease in a second direction within a limited range so as to accommodate different sizes of heads of patients while the constituent blocks are allowed to move in the first direction.

Preferably, the snap-in connectors are configured as a combination of a sliding block and a sliding chute, wherein the sliding block is provided with at least one extension component that is configured to extend or retract within a limited range, and the sliding block and the sliding chute provided on the adjacent constituent blocks are configured to engage with and positionally restrict each other, so that the constituent blocks, under limited movable positional restriction of the extension component, are able to increase or decrease the distance between the adjacent constituent blocks in the second direction in the limited range to accommodate the different sizes of the heads of the patients, and to slide in the first direction along a sliding path defined by the sliding block and the sliding chute that are arranged along the first direction.

Preferably, the drive system at least comprises a driving device, a rotating device, and a connecting rod, wherein the driving device arranged in at least a partial region of the second unit is transmissibly connected to one end of the connecting rod, while an opposite end of the connecting rod extends to the first unit in a direction from the second unit to the first unit and is rotatably connected to the rotating device provided in the first unit to form the drive system, and the drive system serves to transmit a force generated by the driving device to the rotating device through the connecting rod, so that the rotating device receiving the force drives the first unit to move upward or downward with respect to the second unit.

Preferably, the rotating device comprises a damping shaft and a base, wherein the damping shaft connected to one end of the connecting rod is fixed to the base through at least one fixing point provided on the base, while a different part of the base is connected to the first unit, so that the damping shaft is configured to be driven by the force that is transmitted by the connecting rod and drive the base and further the first unit to move upward or downward with respect to the second unit.

Preferably, the constituent block further comprises a detecting device, wherein the first unit and the second unit are provided at least one said detecting device therein, so that a distance value between at least one of the first unit and the second unit and the EEG measuring area on the head of the patient is configured to be detected by the detecting device.

Preferably, the constituent block further comprises a drive controlling device electrically connected to the detecting device, and the drive controlling device is further electrically connected to the driving device, so that a distance value measured by the detecting device is configured to be at least transmitted to the drive controlling device, or so that the drive controlling device is configured to at least transmit an electrical signal to the driving device, thereby changing operational parameters of the driving device.

Preferably, the EEG cap further comprises a housing, earflaps, rotating members, and a VR face shield, wherein the earflaps are formed integratedly with the housing and at positions on two side of the housing symmetrically and close to ears of the patient, and at least two said rotating members are respectively arranged on outer walls of the earflaps in directions outward offset from axes of the earflaps, rotatable support blocks connected to the at least two rotating members are rotatably connected to at least two terminals of the VR face shield, respectively, so that the VR face shield is configured to rotate clockwise or anticlockwise along a curved outer direction of the head of the patient without contacting the housing and the cap body.

Preferably, the EEG cap further comprises an electronic switch and an ultraviolet lamp, wherein data ports are provided in at least one partial region of the housing, and the data ports are connected to a data transmitting module that is installed in at least one nearby partial region of the housing, wherein the data transmitting module is electrically connected to the VR face shield, the drive controlling device, and the electronic switch, and the electronic switch is provided on a power supply loop for the ultraviolet lamp installed inside the housing.

Preferably, the EEG cap further comprises: a hair-moving portion, for pushing hairs in an area of a scalp of the patient that contact the extracranial electrode aside, wherein at least one said hair-moving portion configured to move with the extracranial electrode is installed in at least one partial region of the extracranial electrode, wherein the hair-moving portion is configured to at least expand and/or retract in a direction perpendicular to the extracranial electrode as the extracranial electrode rotates, thereby moving hairs near a contacting point between the extracranial electrode and an EEG measuring area and/or pulling hairs near a contacting point between the extracranial electrode and an EEG measuring area in a direction of an axis of the extracranial electrode as the extracranial electrode moves axially.

The present invention provides the following advantages:

The EEG cap of the present invention is of an assembled, downward-pressing, modular structure, and can be independently driven in an intelligent way according to practical research needs and medical needs. Its VR face shield serves to block external visual interference and to allow transformation as well as transmission between patient EEG information and external visualized information. Its porous and light-weight housing further protects the patient head and uses the vias at its surface to allow connection of the electrodes while reducing the weight and increasing ventilation of the cap. The ultraviolet germicidal lamp installed in the porous housing optionally sterilizes components within the porous housing. The data port located at the lower end of the cap body is provided for receipt and transmission of information.

1: cap body; 2: constituent block; 3: driving device; 4: rotating device; 5: first unit; 6: second unit; 7: sliding chute; 8: sliding block; 9: detecting device; 10: drive controlling device; 11: housing; 12: earflaps; 13: rotating members; 14: VR face shield; 15: support blocks; 16: data port; 17: data transmitting module; 18: ultraviolet lamps; 19: drive system; 20: interlocking structure; 21: extracranial electrodes; 22: connecting rod; 23: hair-moving portion; 24: electrode-fixing plate; 25: electrical impedance sensor; 26: connecting member; 27: first connecting surface; 28: second connecting surface; 29: first contacting point; 30: second contacting point; 31: contacting surface; 32: damping shaft; 33: base.

DETAILED DESCRIPTION OF THE INVENTION

In the description of the present invention, the terms "first", "second", and "third" are only used for descriptive purposes, and cannot be understood as indicating or implying relative importance or implicitly indicating the number of indicated technical features. Thus, the features defined as "first", "second", and "third" may explicitly or implicitly include one or more of these features. In the description of the present invention, "plurality" means two or more than two, unless otherwise specifically defined.

In the description of the present invention, it needs to be understood that if not specifically limited, the orientation or positional relationship indicated by the terms "center", "longitudinal", "lateral", "length", "width", "thickness", "upper", "lower", "front", "back", "left", "right", "vertical", "horizontal", "top", "bottom", "inner", "outer", "clockwise", "counterclockwise", "inner side" and "internal" are based on the orientation or positional relationship shown in the drawings, which is only for the convenience of describing the present invention and simplifying the description, and does not indicate or imply the device or element referred to that it must have a specific orientation, be constructed and operated in a specific orientation, and therefore cannot be understood as a limitation of the present invention.

In the present invention, unless otherwise clearly specified and defined, the terms "installed", "linked", "connected", "fixed" and other terms should be understood in a broad sense, for example, it can be a fixed connection or a detachable connection, or an integral connection; it can be a mechanical connection or an electrical connection; it can be directly connected or indirectly connected through an intermediate medium, and it can be the internal connection between two components. For those of ordinary skill in the art, the specific meaning of the above-mentioned terms in the present invention can be understood according to specific circumstances.

Figure 2:
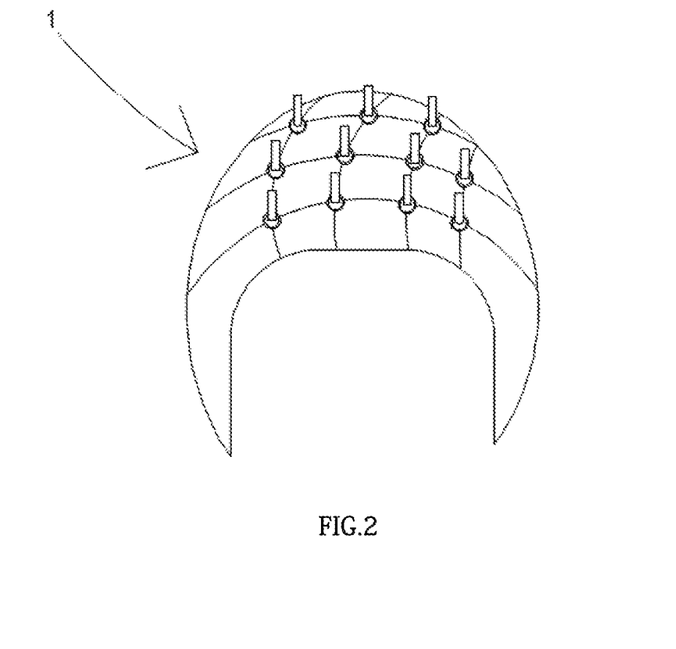
FIG. 2 is a schematic drawing of a cap body of the EEG cap.
Figure 3:
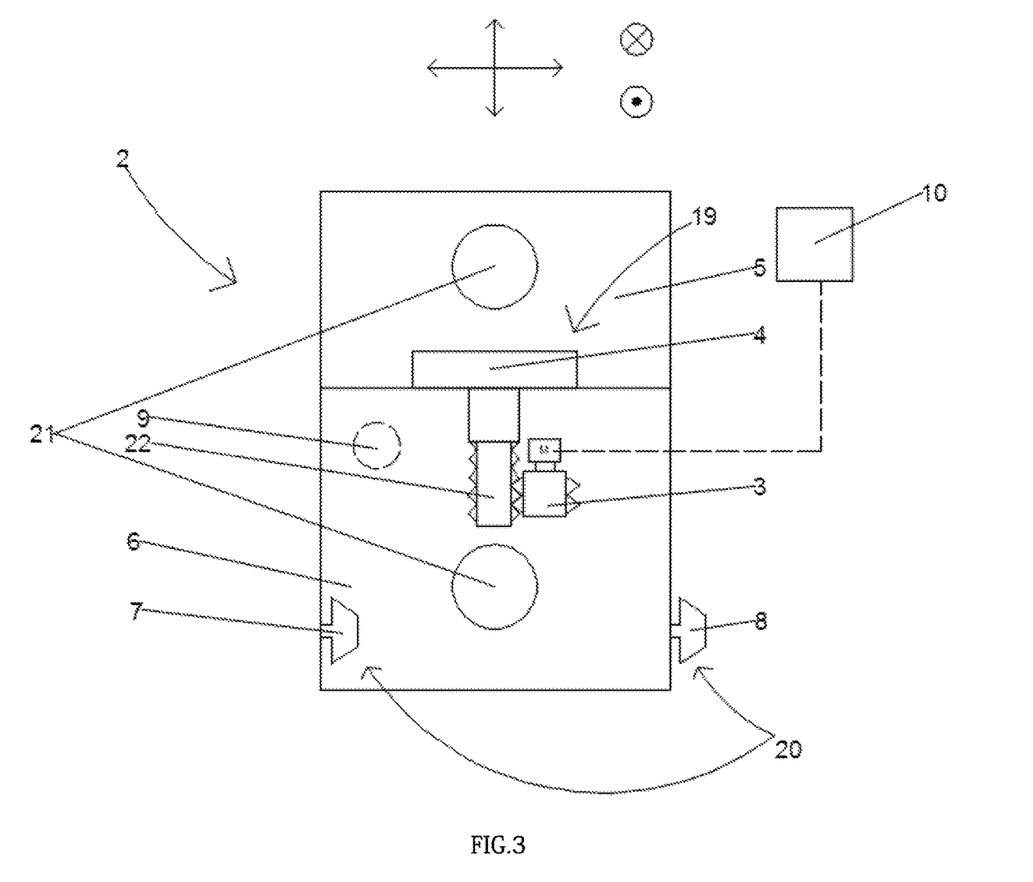
FIG. 3 is a schematic top view of a constituent block of the EEG cap.

The present invention relates to an assembled, downward-pressing, multifunctional EEG cap, comprising a cap body 1 (as shown in FIG. 2) that is formed by basic units that are rotatably connected to each other. To state differently, the present invention divides the traditional one-piece EEG cap covering the EEG measuring area on the head of the patient into a plurality of basic units that are configured to move vertically with respect to each other. Each of the basic units is formed with at least one electrode via communicating the exterior with the surface of the head of the patient so that the extracranial electrodes 21 can be installed on the basic units through the electrode vias and aligned with the EEG measuring area on the head of the patient. Since many of the basic units are similar in terms of structure and function, the following description will be focused on a single constituent block 2 formed by two adjacent basic units as shown in FIG. 3, which includes a first unit 5, a second unit 6, and a drive system 19. It is to be noted that the first unit 5 and the second unit 6 are both basic units that to be fit on the head of the patient, and they are of no difference at least in terms of carrying the extracranial electrodes 21. They are differentiated herein only for easy illustration of relative movement between two adjacent basic unit.

In order to clearly explain the relationship among the first unit 5, the second unit 6, and other mechanisms connected thereto in terms of relative displacement direction on the head of the patient, a first direction is defined as the direction of moving toward or away from the EEG measuring area on the head of the patient (i.e., some sites on the human scalp), which is the direction perpendicular to the plane of the schematic top view of the constituent block as shown in FIG. 3, and a second direction is defined as the direction along the curved surface of the head of the patient, which is the cross direction as represented in FIG. 3, the schematic top view of the constituent block.

The constituent block has at least an interlocking structure 20 that is provided at the periphery of the first unit 5 or the second unit 6 and extend along the first direction. The interlocking structure 20, when receiving an external force, can move upward or downward with respect to the adjacent constituent block(s) 2 and can expand or retract within a limited range so as to move for a distance along the second direction. The interlocking structure 20 may be a combination of a sliding block 8 and a sliding chute 7. The sliding block 8 has a surface contacting the sliding chute 7 formed for form-fit, and may have a special shape, such as an arrow with its shaft smaller than its head, so that the sliding block 8 is allowed to move upward and downward freely in the sliding chute 7 and is prevented from move transversely along the direction of the curved surface of the head of the patient. Specifically, the direction in which the constituent block 2 move upward and downward with respect to its adjacent constituent block(s) 2 is the first direction.

At the joint between the sliding block 8 and the basic unit, there is an extension component configured to extend or retract within a limited range. For example, the extension component may be an accordion-like folded structure or a linear structure formed by an elastic rope or the like, so that the constituent blocks 2 connected through the sliding block 8 and the sliding chute 7 can come close to or go away from each other within a limited range in the direction of the curved surface of the head of the patient.

In virtue of the interlocking structure 20, when the disclosed EEG cap is worn by different patients, the distance between the adjacent constituent blocks 2 can increase or decrease within a limited range along the curved surface of the head of the patient for accommodating the head size of the present user. Since the increase or decrease is limited, the integrity of the shape of the cap can be held without the risk of falling into pieces. In addition, since the sliding block 8 can freely slide in the sliding chute 7 along the first direction, the user can easily add or remove individual constituent blocks 2 to or from the cap body, thereby conveniently replacing or repairing any broken constituent block 2.

The number and locations of the basic units are reasonably planned according to the electrode layout of the EEG cap, so that a basic unit is retained in position with respect to its adjacent basic unit(s) by at least one combination of its sliding chute 7 or sliding block 8 and the sliding chute(s) 7 or sliding block(s) 8 of the adjacent basic unit(s).

The drive system 19 comprises a driving device 3, a rotating device 4, and a connecting rod 22. The driving device 3 is installed in at least a part of the second unit 6 by means of screw fixation and serves to provide a mechanical force that drives the basic unit to move.

The connecting rod 22 is installed near the driving device 3 in the at least one part of the second unit 6, and has at least a part of its rod body formed with threads while the rest of the rod body has a smooth surface. The connecting rod 22 extends to the joint between the second unit and the first unit along a central axis passing through the first unit and the second unit and is rotatably connected to the rotating device 4 located at the corresponding edge of the first unit. The threaded shaft of the driving device 3 extending along the direction of the connecting rod 22 and parallel to and near the connecting rod 22 is configured to engage with the threaded structure of the connecting rod 22, so that when it is necessary to move the basic unit upward or downward, the driving device 3 is powered to drive the rotational shaft to rotate clockwise or anticlockwise and in turn drive the connecting rod 22 to move forward and backward along the direction of the connecting rod 22 by means of the threaded engagement.

The driving device 3 may be any kind of power-driven motors or electromagnetic induction motors. According to a preferred mode, the driving device 3 is a micro step motor. The motor can precisely control its step angle (the rotational angle of the motor shaft), and may have a size as small as about 8 mm. Such a motor can typically provide a torque of about 300 mN·m (depending on the actual model used) and precisely move the connecting rod 22 to the present position along the installation direction of the connecting rod 22 through the threaded engagement of the external threads, thereby achieving control of the relative distance or location between the first unit 5 and the second unit 6. The thread mechanism is well designed so that the axial threaded engagement effectively prevents overheat caused by motor overload. To be more detailed, after the motor stops, the external threads of the connecting rod 22 and the external threads of the motor are engaged in a snap-like way, thereby limiting the distance between the first unit 5 and the second unit 6 to a predetermined range.

The foregoing transmission structure in practice is not limited to threaded engagement. Instead, it may be alternatively realized using belt-based transmission or gear-based transmission, as long as the connecting rod 22 is allowed to perform present movement along its installation direction in response to an external force.

Figure 4:
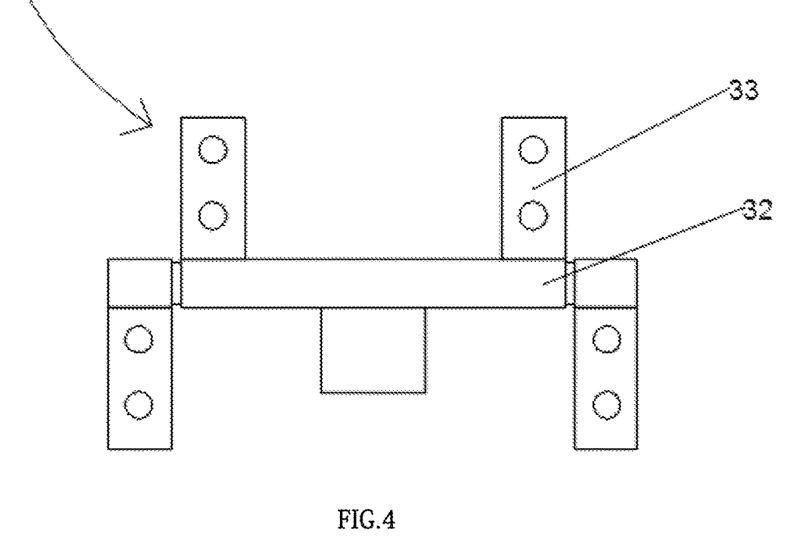
FIG. 4 is a schematic drawing of a rotating device of the EEG cap.

The rotating device 4 located at the corresponding edge of the first unit 5 (as shown in FIG. 4) at least comprises a base 33 and a damping shaft 32. The base 33 may be integratedly formed with or screw-fixed to the damping shaft 32, and may be screw-fixed to the edge of the first unit 5. The base is such oriented that the damping shaft 32 is parallel to the edge line of the first unit 5. The damping shaft 32 may have at least one part thereof integratedly formed with or detachably screwed with a connecting end. The connecting end may be fixed to one end of the connecting rod 22 that is far away from the area interacting with the micro step motor by means of welding. Preferably, the connecting end of the damping shaft 32 may be detachably fixed to the connecting rod 22 using a combination of a screw rod and a threaded through hole, so that any damaged or broken basic unit can be easily detached for replacement or repairment.

Preferably, the connecting rod 22 installed in the second unit 6 may have a ballscrew structure. The ballscrew structure at least comprises a screw shaft, a ball nut, and a ball. The screw shaft has two ends thereof, in the axial direction of the second unit 6 and the first unit 5, fixed to rotatory tables on the second unit 6 and the first unit 5, respectively. The ball nut is provided on the threaded structure of the screw shaft. The outer side of the ball nut that is not connected to the screw shaft is fixed (by means of welding, for example) or detachably connected (by means of a threaded structure, for example) to the connecting end of the damping shaft 32 incorporated by the rotating device 4 in the first unit 5. The micro step motor rotates the screw shaft by means of threaded engagement transmission, and in turn makes the ball nut drive the connecting end to move forward and backward along the installation direction of the screw shaft.

Thus, in the present embodiment, the transmission process performed on the cap body 1 is that, the driving device 3, which may be a micro step motor, installed on the second unit 6 is activated to make the rotational shaft of the micro step motor rotate clockwise or anticlockwise, and then one end of the connecting rod 22 parallel to and threadedly engaged with the nearby rotational shaft is driven to rotate by the rotation of the rotational shaft. Afterward, the ballscrew or similar structure on the connecting rod 22 converts the rotational force at one end of the connecting rod 22 into a push-and-pull force in the radial direction of the connecting rod 22 to forward push or backward pull the rotational structure connected to the opposite end of the connecting rod 22. The rotational structure having its opposite end fixed to the first unit 5 responds to the push or pull force to drive the first unit 5 to move upward or downward with respect to the second unit 6. Since the extracranial electrodes 21 are separately installed on the first unit 5 and the second unit 6, their distances to the EEG measuring area on the head of the patient can be adjusted independently.

The drive controlling device 10 located near the driving device 3 is electrically connected the signal receiving end of the driving device 3 through a wire or a wireless communication module, and serves to send an adjustment instruction in the form of an electrical signal to the driving device 3 when there is a need for adjusting operational parameters of the driving device 3, such as its power or step angle.

To measure and record the distance between each basic unit and the scalp (i.e., the EEG measuring area on the human scalp) of the patient wearing the cap body 1, a detecting device 9 may be provided in each individual basic unit. It serves to transmit the measured distance data together with identity codes pre-assigned to the units to the drive controlling device 10. Then the distance data is transmitted to the exterior through the electric connection between the drive controlling device 10 and the data transmitting module 17. The detecting device 9 may be a distance measuring device such as an ultrasonic rangefinder or the like. Its working principle is that when an ultrasonic wave emitted by the detecting device hits the human scalp, it reflects. The time from emission of the ultrasonic wave to receipt of the back wave is processed using scientific computation, so as to figure out the distance between the detector and the human scalp, which indicates the distance between the basic unit and the human scalp. As a simpler approach, by well designing the transmission relationship among the driving device 3, the connecting rod 22, and the rotating device 4, a relation equation between the motion scale of the driving device 3 (such as turns of the rotational shaft of the motor) and the motion scale of the first unit 5 with respect to the second unit 6 driven by the rotating device (such as the distance of the relative upward and/or downward movement) can be found through scientific deduction or a limited number of experiments. Accordingly, by measuring the motion scale of the driving device 3, the motion scale of the first unit 5 with respect to the second unit 6 can be determined indirectly. The data obtained using the two measuring methods discussed previously can at least be used to control the distance of the upward and downward movement of the first unit 5 with respect to the second unit 6.

Figure 1:
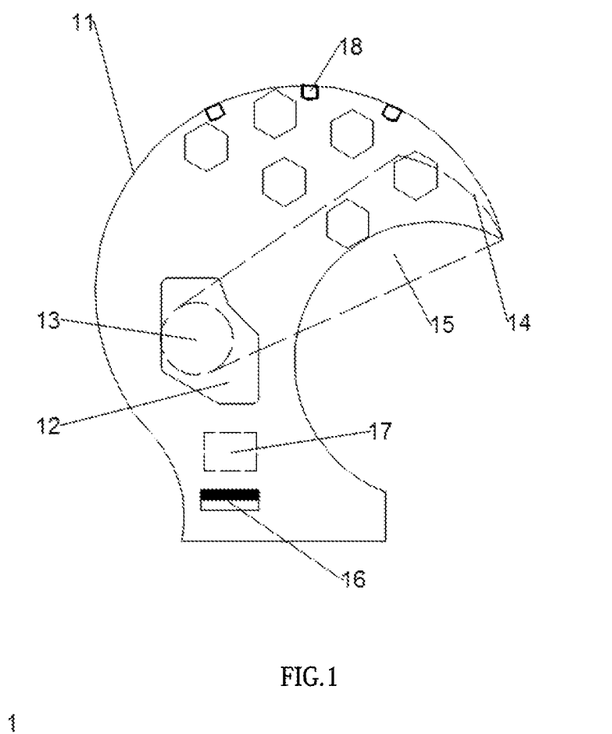
FIG. 1 is a schematic drawing of an assembled, downward-pressing, multifunctional EEG cap of the present invention.

The disclosed EEG cap (as shown in FIG. 1) further comprises a VR face shield 14, a cap body 1, a housing 11, an ultraviolet lamp 18, and a data port 16.

The cap body 1 that is used to wrap the head of the measured subject (or the user, or the patient) in a non-contact or partial-contact manner for EEG measurement is shaped and sized according to an average head of the patient. Additionally, for reducing its weight, for adding ventilation feeling to the measured subject, and for easy installation of the electrodes to the electrode vias arranged on the cap body 1 from outside, a housing 11 is provided to protect the assembled, downward-pressing, EEG cap received therein. The housing 11 has irregular polygonal holes that are mechanically made to align with the individual electrode vias and are perpendicular to the direction of the round surface of the electrode vias direction, with their opening area slightly greater than the round opening area of the electrode via. Meanwhile, the housing 11 may be made of rigid plastic, such as high-density polyethylene or fiberglass, so as to be lightweight and comfortable to wear.

The housing 11 that protects the cap body 1 has two earflaps 12 symmetrical about the centerline of the head of the patient and corresponding to two laterals of the head of the patient for completely covering human ears. The earflaps 12 are integratedly formed on the protective housing and are sized to accommodate average human ears. The earflaps 12 are raised from the profile of the housing 11, so as to form sound-isolating chambers inside the housing 11. The sound-isolating chambers are internally equipped with high-performance soundproof material, such as acoustical foam or acoustic baffle. Thereby, when the measured subject wears the novel EEG cap, the external noise can be blocked out, so as to prevent the measured subject undergoing EEG measurement from noise.

On the housing 11 that protects the cap body 1, there is a VR face shield 14 that is centrally located to positionally correspond to human eyes for completely obstructing eyeshot. The VR face shield 14 has two support blocks 15 welded or screwed to two sides of the housing 11 near the ear positions. The two support blocks 15 each have an opposite end snap-engaged with two rotating members 13 that are welded or screwed to the outer sides of the earflaps 12 inside the housing 11 in a direction coaxial with the earflaps 12, so that the VR face shield 14 can be moved by an external force (such as operated mutually) in the direction clockwise or anticlockwise direction along the curved shape of the head of the patient, so as to selectively cover the eyes. Additionally, the VR face shield 14 is equipped with a display device, such as a digital display, at the side facing the eyes of the measured subject. The display device serves to show the measured subject video or visual instruction information. The VR face shield 14 has its side back to the eyes of the measured subject made of an opaque material, so as to prevent the measured subject from external disturbing visual information.

One or more ultraviolet lamps 18 are adhered or screwed to the upper, inner wall of the housing 11 at areas without the polygonal holes and corresponding to the head of the patient. The ultraviolet lamps are arranged into a predetermined pattern so that the emitted UV light can fully cover the cap body 1. The power cords of all these ultraviolet lamps 18 are fixed to the curved inner surface of the protective housing by means of, for example, adhesive, and are collected and connected to the electronic switch near the data transmitting module 17. When the electronic switch receives an activation instruction from the data transmitting module 17, it closes the circuits of the ultraviolet lamps 18, so that the ultraviolet lamps 18 are powered and illuminate. The UV light is used to sterilize the interior of the housing 11 before and/or after EEG measurement.

A data transmitting module 17 is adhered or screwed to the lower part of the housing 11 corresponding to the human neck. A small rectangular opening is mechanically made on the housing near the data transmitting module 17. A data port 16 is installed by means of adhesion or welding in the small rectangular opening. The opposite end of the data port 16 is a data output end, which is connected to the input end of the data transmitting module 17 through connection of a wire and an input terminal. The data transmitting module 17 has its signal output end wired to the data port of the VR face shield 14 device, the data receiving end of the drive controlling device 10 on the cap body 1, and the electronic switch, respectively. When receiving signals form the data port 16, the data transmitting module 17 uses a single-chip microcomputer integrated in its circuit to determine the contents of the signals and optionally performs the following operations accordingly.

When the data transmitting module 17 receives personal information of a measured subject from the exterior through the data port 16 (such as information on the pressures at individual regions or on the relative positions of the basic units collected when the measured subject used the cap body 1 of the disclosed multifunctional EEG cap last time), the pressure information or relative position information can be transmitted to the drive controlling device 10 of the cap body 1 through the electrical connection between the cap body 1 and the drive controlling device 10 so as to help the drive controlling device 10 control the operational parameters of the driving device 3 inside the cap body 1, thereby adapting the downward-pressing position of the EEG cap according to the pressure information or relative position information specific to a certain measured subject collected when the measured subject used the novel EEG cap last time, and ensuring good fit between the EEG cap and the head of the measured subject.

When the data transmitting module 17 receives video data information from the exterior through the data port 16 (such as visual testing information or visual communication instruction information the measurement conductor wants to show the measured subject), the video data information can be transmitted to the VR face shield 14 through the electrical connection to the data receiving port of the VR face shield 14, so that after receiving the video data information, the VR face shield 14 can show the video data on the display device facing the eyes of the measured subject, thereby accomplishing some EEG measurement based on the visual nervous system of the measured subject or allowing the measurement conductor to first block any external interference and then send visual instruction to the measured subject.

When the data transmitting module 17 receives instruction to turn on or turn off the electronic switch from the exterior through the data port 16, the instruction to turn on or turn off the electronic switch can be transmitted through the electrical connection to the electronic switch, so as to control the electronic switch and in turn activate or deactivate the ultraviolet lamps 18 installed at the upper part of the housing 11, thereby selectively sterilizing the components inside the disclosed EEG cap.

By using the detecting device 9, the data transmitting module 17, the drive controlling device 10, and the driving device 3 together, the data about the downward-pressing distance of the basic units to the scalp collected when the patient used the disclosed EEG cap for the first time and recorded in the storage system built in the EEG cap or transmitted through the data port 16 to a device external to the EEG cap can be retrieved for later use. As a result, when the same patient wants to use the EEG cap again, the downward-pressing parameter can be automatically or manually transmitted through the data port 16 or the storage system built in the EEG cap to the data transmitting module 17 together with an identifier of any type. Then the drive controlling device 10 converts the downward-pressing parameter it receives from the data transmitting module 17 into a control instruction to control the operation of the driving device 3, thereby achieving rapid and adaptive downward-pressing adjustment according to records of the head profiles of different patients. This helps save time because the medical staff do not have to make adjustment from the beginning any more, thereby improving working efficiency.

As used to describe the EEG cap of the present invention, the phrase "assembled, downward-pressing" indicates the fact that the cap body 1 is assembled form plural constituent blocks 2 connected to each other by means of the interlocking structure 20 so that in each of the constituent blocks 2, the first unit 5 and the second unit 6 can move with respect to each other in a direction of moving toward or away from the head of the patient when they are driven by the drive system 19 installed therebetween. Such the foregoing configuration, every basic unit can be pressed downward independently. Also as used to describe the EEG cap of the present invention, the term "the multifunctional" indicates the fact that in addition to the foregoing functions about assembling and downward-pressing, the EEG cap further has the functions of using the VR face shield 14 to block the patient from the external visual information to transmit visual information, the function of using the earflaps 12 to block the patient from external acoustic information, the function of using the data transmitting module 17 to transmit video data and pressure data, the function of using switch to turning on or off the ultraviolet lamps 18, and the function of using the ultraviolet lamps 18 for sterilization.

The data transmitting module and drive controlling device used in the present invention may be made of a single-chip microcomputer, such as one modeled STM32F051C8T6, or a PLC having similar functions or circuit design, for the advantages in terms of simple structure and compact size. Additionally, the electronic switch for turning on or off the ultraviolet lamp 18 of the present invention may be made of a micro relay, such as one from OMRON, modeled G5V-1. The foregoing data chip and electronic switch are both known in the art, and the control process involved by the present invention may be realized using simple component design.

In use of the novel EEG cap of the present invention, a patient (also referred to a user or a measured subject herein) first puts on the cap, and if this is the first time the patient uses the disclosed EEG cap, he/she shall then adjust the downward-pressing state of the cap body 1. If the patient has used the disclosed the EEG cap before, he/she may retrieve the downward-pressing parameter associated to his/her last use of the cap through the data port 16. The parameter data is thus transmitted by the data transmitting module 17 to the drive controlling device 10 and to the electrical signal control line of the driving device 3 and the driving device 3, thereby controlling the downward-pressing parameter of the driving device 3. Thus, the cap body 1 can be pressed downward to a position specific to the patient, and the medical staff can set out to EEG measurement after performing fine tuning on this basis. For a patient who uses the EEG cap for the first time, the adjustment is performed as below. The medical staff control the downward-pressing parameter of the cap body 1 according to factors such as the head size and profile of the patient, the length of the extracranial electrodes 21 or the pretest intensity of EEG signals through the data path so as to more reasonably fit the cap body 1 to the patient head. At least some parts of the foregoing adjustment can be done automatically using process control, so as to minimize the labor work from the medical staff. After the cap body is adjusted, the detecting device installed inside the cap body 1 can measure the distance between the cap body 1 and the patient head, and transmits the parameter through the electrical signal path connected to the data port 16 for storage as reference of the downward-pressing parameter for the patient when he/she uses the disclosed EEG cap next time. Afterward, the medical staff or the patient turns the VR face shield 14 down along the curved surface of the patient head, so that VR face shield 14 blocks the patient from the external visual interference. Meanwhile, with the earflaps 12 of the disclosed EEG cap, the patient can be protected from the ambient disturbing sounds. When it is desired to transmit visual information to the patient for vision-related EEG measurement or to send an instruction to the patient, the medical staff may send video information to the VR face shield 14 through the electrical signal path connected to the data port 16. Before or after use of the disclosed EEG cap, the medical staff can selectively activate the ultraviolet lamp 18 installed within the EEG cap housing 11 through the electrical signal path connected to the data port 16, thereby sterilizing the interior of the EEG cap.

Figure 5:
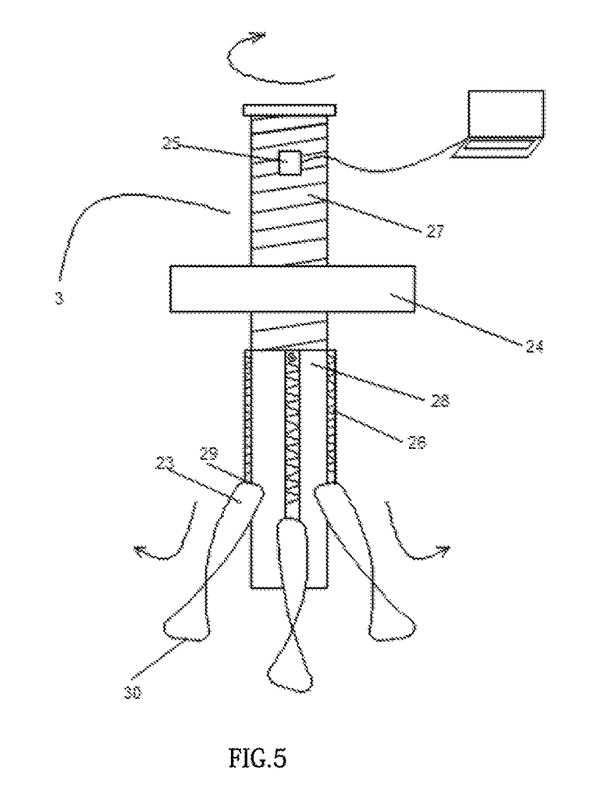
FIG. 5 is a plane view of an extracranial electrode of the EEG cap.

The extracranial electrode 21 of the present invention further comprises one of the following components: a hair-moving portion 23, an electrode-fixing plate 24, and an electrical impedance sensor 25. The extracranial electrode 21 (as shown in FIG. 5) detachably connected to the electrode via on the cap body 1 through the electrode-fixing plate 24. At least one electrical impedance sensor 25 is locally provided at the periphery of the extracranial electrode 21 for measuring resistance of the extracranial electrode. In at least one partial region of the extracranial electrode, there is at least one hair-moving portion 23 configured to move with the extracranial electrode 21.

According to a preferred implementation mode, plural roughly round electrode-fixing plates 24 are attached to the outer lateral of cap body 1 of the EEG cap opposite to the patient head and right over the plural round electrode vias by means of, for example, adhesion.

Figure 6:
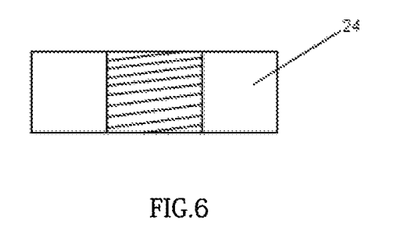
FIG. 6 is a cross-sectional view of an electrode-fixing plate of the EEG cap.

Preferably, the roughly round electrode-fixing plate 24 (as shown in FIG. 6) defines therein a roughly ring-like chamber. The chamber acts as a connecting channel for the extracranial electrode 21 to contact the corresponding EEG measuring area on the patient head. The electrode-fixing plate 24 at its inner wall that contacts and connects the extracranial electrode 21 is provided with a threaded structure. When the EEG cap is in a stand-by mode or in an operation mode, by virtue of the threaded structure between the inner wall of the electrode-fixing plate 24 and the peripheral outer lateral of the extracranial electrode 21, non-fixed, adjustable connection between the extracranial electrode 21 and the cap body 1 of the EEG cap can be achieved.

According to a preferred implementation mode, a roughly columnar, adjustable multifunctional extracranial electrode 21 is located in the chamber of the electrode-fixing plate 24 adhered right over the corresponding round electrode via on the outer surface of the cap body 1 of the EEG cap. The extracranial electrode 21 is installed in a direction perpendicular to the chamber by means of a threaded structure. The peripheral outer wall of the extracranial electrode 21 goes outward to enter the electrode via. The extracranial electrode 21 has a semi-thread structure extending in an up-to-down direction. A first connecting surface 27 in the form of a threaded surface is formed in at least one partial region of the peripheral outer lateral of the extracranial electrode 21. The rest may be formed as a second connecting surface 28 in the form of, for example, a plane surface.

Preferably, the extracranial electrode 21 and the electrode-fixing plate 24 are connected through the threaded structure on the first connecting surface 27, and the threaded structure allows orientational adjustment of the extracranial electrode 21 so as to be adaptive to the diverse patient-specific needs for EEG signal collection during practical measurement and to improve use comfort for patients. Specifically, by rotating the extracranial electrode 21 clockwise and/or anticlockwise, the extracranial electrode 21 is moved downward and passes through the electrode-fixing plate 24 so that the extracranial electrode 21 is fixed within the electrode via. By reversely rotating the extracranial electrode 21, the extracranial electrode 21 is pulled out from the electrode-fixing plate 24 and leaves the electrode via. The extracranial electrode 21 collects EEG signals mainly through its contact with the corresponding EEG measuring area on the patient head, and transmits the collected EEG signals in the form of electrical signals to an external EEG-signal collecting device connected to the circuit of the extracranial electrode 21.

According to a preferred implementation mode, on the extracranial electrode 21 having the roughly columnar shape and having the semi-threaded structure at the peripheral outer lateral of its outer wall, plural hair-moving portions 23 are connected to through the connecting member 26 the second connecting surface 28 that extend from up to down along its axis at the peripheral outer lateral of the bottom. The plural hair-moving portions 23 are arranged in an equidistant manner and move with the extracranial electrode 21.

Figure 7:
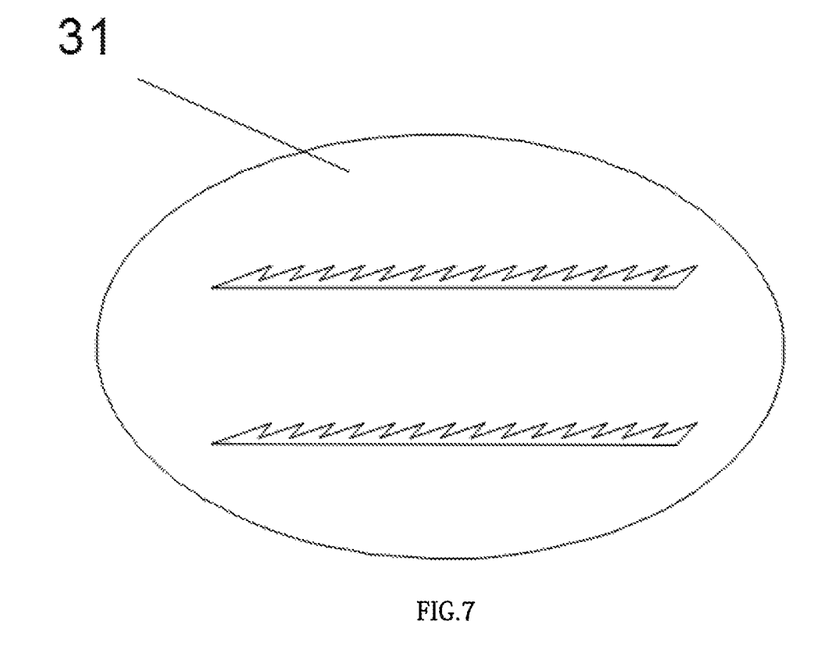
FIG. 7 is a partial, schematic drawing of a hair-moving portion of the EEG cap.

Preferably, the hair-moving portion 23 has a curved, twisted shape. Its upper end near the extracranial electrode 21 is formed with a first contacting point 29 that is connected to the connecting member 26. Its lower end has a second contacting point 30 configured to contact the patient scalp. The second contacting point 30 is provide with a smooth edge, so as to minimize its irritation to the patient head. Meanwhile, the curved, twisted structure adds sliding friction when the hair-moving portion 23 contacts the patient hairs, thereby minimizing relative displacement between patient hairs and the hair-moving portion 23 that may appear when the hair-moving portion 23 rotates, and in turn increasing the hair-moving area of the hair-moving portion 23, so as to enhance hair-moving efficiency.

Preferably, the hair-moving portion 23 may have the contacting surface 31 that least one side contacting the patient head provided with at least one irregular feature, such as particles, waved texture and/or teeth, which that are known by people skilled in the art to be effective in increasing surface friction (as shown in FIG. 7). The features are for increasing the sliding friction between the patient hairs and the hair-moving portion 23, so that the patient hairs when contacting the surface of the hair-moving portion 23 can be pushed aside, thereby ensuring good contact between the extracranial electrode 21 and the corresponding EEG measuring area on the patient scalp.

Preferably, the hair-moving portion 23 is made of rubber and/or plastic that absorb no water and/or oil or other materials having the same or similar nature, so as to prevent the hair-moving portion 23 from becoming less frictional as the patient scalp secretes sweat and/or oil over time.

According to one preferred implementation mode, the hair-moving portion 23 is for example hinged to at least one partial region of the second connecting surface 28 at the peripheral outer side of the extracranial electrode 21. In addition, the extracranial electrode 21 is axially connected to the hair-moving portion 23 through the connecting member 26 to form a transmission structure. The transmission structure through a force transmission form known to people skilled in the art, such as mechanical transmission and/or electromagnetic driving force, to make the hair-moving portion 23 move with and with respect to the extracranial electrode 21. Specifically, when the extracranial electrode 21 is not used, the hair-moving portions 23 are retracted about the axis of the extracranial electrode 4 and gathered around the axial outside at the bottom of the extracranial electrode 21. When the extracranial electrode 21 is rotated clockwise and/or anticlockwise to be inserted downward vertically into the electrode via, the transmission mechanism arranged between the extracranial electrode 21 and the hair-moving portions 23 in turn drives the hair-moving portions 23 to rotate. In other words, when the extracranial electrode 21 rotates clockwise and/or anticlockwise and moves downward, the hair-moving portions 23 rotate clockwise and/or anticlockwise about the axis of the extracranial electrode 21 and expand simultaneously like blooming petals, thereby pushing the hairs around the extracranial electrode 21 aside. When the extracranial electrode 21 is rotated clockwise and/or anticlockwise and vertically pulled out from the electrode via, the transmission mechanism between the extracranial electrode 21 and the connecting surface of the hair-moving portion 23 in turn drives the hair-moving portions 23 to rotate. In other words, when the extracranial electrode 21 rotates clockwise and/or anticlockwise and moves upward, the hair-moving portions 23 rotate clockwise and/or anticlockwise to be are retracted simultaneously about the axis of the extracranial electrode 21, thereby allowing the extracranial electrode 21 to be removed from the electrode via smoothly.

According to a preferred implementation mode, on the peripheral outer lateral at the top of the adjustable, multifunctional extracranial electrode 21 that is roughly columnar in shape and having the semi-threaded structure at the peripheral outer side of its outer wall, there is an impedance detecting and reporting device serves to measure and feedback the measured resistance value at the extracranial electrode.

Preferably, at least one electrical impedance sensor 25 of the impedance detecting and reporting device is detachably connected to the peripheral outer lateral of the extracranial electrode 21. The electrical impedance sensor 25 is connected to the circuit of an external controlling and identifying device. The electrical impedance sensor 25 serves to measure and feedback the resistance at the extracranial electrode 21 in a real-time manner. With the electrical impedance sensors 25, during EEG signal collection, the operational states of individual extracranial electrodes can be determined according to their real-time variations in resistance, so that the incompliant extracranial electrodes can be targeted and adjusted in impedance and/or conductive gel can be optionally added and use amount can be modified to maintain accurate EEG signal collection.

In use of the extracranial electrode 21 of the present invention, the cap body 1 is first placed on the corresponding area on the patient head as instructed. Then the extracranial electrodes 21 that serve to collect EEG signals and have electrical impedance sensors 25 at their surfaces are installed into the electrode vias on the cap body through the electrode-fixing plates 24. The fit between electrode-fixing plate 24 and the extracranial electrode 21 is used to adjust the distance between the extracranial electrode 21 and the EEG measuring area on the patient head, thereby adjusting the function of the extracranial electrode 21. When the distance between the extracranial electrode 21 and the EEG measuring area on the patient head is adjusted, the hair-moving portions 23 provided in partial regions of the extracranial electrodes 21 expand outward and/or retract inward about their rotational axes in response to the rotation of the extracranial electrodes. For example, when the extracranial electrode is rotated clockwise, the hair-moving portion 23 at its bottom can gradually expand about the extracranial electrode 21 to push the nearby patient hairs aside. When the extracranial electrode 21 is rotated anticlockwise, the hair-moving portion 23 at its bottom can gradually retract about the extracranial electrode 21 to restore the patient hairs, thereby allowing the extracranial electrode 21 to be removed from the electrode via on the cap body 1 easily. In addition, at least one electrical impedance sensor 26 is provided locally on the extracranial electrode 21 and connected to the circuit of an external controlling and identifying device for measuring and reporting the resistance value in a real-time manner. In some preferred embodiments, the electrical impedance sensor 26 and the data transmitting module 17 are electrically connected to each other. An external device or the data transmitting module 17 itself can feed the resistance information collected by the electrical impedance sensor 26 back to the drive controlling device to control the downward-pressing operation of separate constituent block, so as to make the overall downward-pressing adjustment more accurate.

To sum up, the extracranial electrode 21 as disclosed in the present invention is designed to have orientational adjustment during EEG signal collection according to practical therapeutic and/or research needs, while eliminating physical interference cause by, for example, patient hairs and ensuring accurate signal collection. Meanwhile, the present invention allows real-time measurement and feedback of resistance values during EEG signal collection, so as to improve the overall accuracy and ultimately realize adjustability and versatileness.

Preferably, the training equipment further includes an EEG cap. The EEG cap adopts a double-track EEG cap, a hairband type, a headband type, asymmetrical type, a skull defect patient-specific, and a lying position-specific and flexible skeleton structure in a way that the cap can be stably and comfortably contacted with the patient, so that the collected signals are stable and accurate, and the signal collection is convenient and comfortable.

Preferably, when the patient is trained through virtual reality technology, the doctor can participate in interactive training and guidance in the virtual scene.

Preferably, the acquisition method of cognition, speech, swallowing, and motion-related signal information is a dual-modal acquisition method that simultaneously acquires EEG and near-infrared signals. This allows researchers to have a more comprehensive and clear understanding of changes in brain function. At the University of California, San Francisco, its scientific research team translates human brain waves into English sentences, with the lowest average error rate as low as 3%, which greatly improves the accuracy of information collection. Near-infrared is considered to be the brain function imaging technology that can meet the above requirements, and provides a new observation method for basic research and clinical application of brain science. As the body's metabolism changes, real-time monitoring can be carried out. By observing these hemodynamic changes, we can speculate on neural activity. Therefore, collecting the patient's brain waves and near-infrared signals can help the system and medical staff to accurately identify the patient's imagination and needs.

Figure 8:
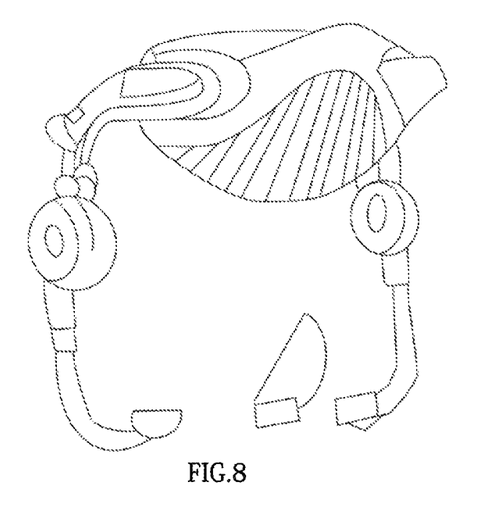
FIG. 8 is a schematic drawing of a preferred embodiment of the EEG cap of the present disclosure.

Preferably, the training equipment further includes an EEG cap. The EEG cap adopts a dual-track EEG cap, a headband type, a headband type, asymmetrical type, a skull defect patient-specific, and a lying position-specific, flexible skeleton structure in a way that the EEG cap can be stably and comfortably contacted with the patient, so that patients with different brain structures, even patients with abnormal brain structures can be provided with comfortable and stable EEG caps, ensuring the stable transmission of EEG signals. The structure of the double-track EEG cap is shown in FIG. 8.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. An assembled, downward-pressing, multifunctional electroencephalogram (EEG) cap, at least comprising:
　a cap body, configured to be worn on a head of a patient, and formed by a plurality of constituent blocks,
　wherein each of the constituent blocks comprises a first unit and a second unit that carry extracranial electrodes for detecting EEG signals from corresponding areas of the head of the patient, in which the first unit and the second unit are configured to perform relative movements and thereby change their relative positions, and
　wherein the constituent blocks comprise snap-in connectors:
　the EEG cap being characterized in:
　for each of the constituent blocks, the first unit and the second unit being shaped to fit a curved surface of the head of the patient; and
　the first unit of the constituent block being movably connected to the second unit by means of a drive system provided between at least a part of the first unit and a part of the second unit,
　wherein the extracranial electrodes located on the first unit and on the second unit are configured to at least follow the relative movements between the first unit and the second unit in a first direction so as to move toward and/or away from an EEG measuring area on the head of the patient, wherein the constituent blocks with snap-in connectors are movably connected with adjacent constituent blocks also provided with snap-in connectors by their respective snap-in connectors, so as to form the cap body and so that when the cap body is put on the head of the patient, a distance between the adjacent constituent blocks is able to increase or decrease in a second direction within a limited range so as to accommodate different sizes of heads of patients while the constituent blocks are allowed to move in the first direction, wherein each snap-in connector is configured as a combination of a sliding block and a sliding chute, wherein the sliding block is provided with an extension component that is configured to extend or retract within a limited range, and the sliding block of one constituent block and the sliding chute provided on an adjacent constituent block are configured to engage with and positionally restrict each other, so that the constituent blocks under limited movable positional restriction of the extension component, are able to increase or decrease the distance between the adjacent constituent blocks in the second direction in the limited range to accommodate the different sizes of the heads of the patients, and to slide in the first direction along a sliding path defined by the sliding block and the sliding chute that are arranged along the first direction.

2. The EEG cap of claim 1, wherein each sliding block has a surface configured to contact a sliding chute formed for form-fit, and has an arrow with its shaft smaller than its head, so that the sliding block is allowed to move upward and downward freely in the sliding chute and is prevented from moving transversely along the direction of the curved surface of the head of the patient.

3. The EEG cap of claim 2, wherein the number and locations of the constituent blocks are planned according to the electrode layout of the EEG cap, so that a constituent block is retained in position with respect to its adjacent constituent block(s) by at least one combination of its sliding chute or sliding block and the sliding chute(s) or sliding block(s) of the adjacent constituent block(s).

4. An assembled, downward-pressing, multifunctional electroencephalogram (EEG) cap, at least comprising:
a cap body, configured to be worn on a head of a patient, and formed by a plurality of constituent blocks,
wherein each of the constituent blocks comprises a first unit and a second unit that carry extracranial electrodes for detecting EEG signals from corresponding areas of the head of the patient, in which the first unit and the second unit are configured to perform relative movements and thereby change their relative positions,
the EEG cap being characterized in:
for each of the constituent blocks, the first unit and the second unit being shaped to fit a curved surface of the head of the patient; the first unit of the constituent block being movably connected to the second unit by means of a drive system provided between at least a part of the first unit and a part of the second unit,
wherein the extracranial electrodes located on the first unit and on the second unit are configured to at least follow the relative movements between the first unit and the second unit in a first direction so as to move toward and/or away from an EEG measuring area on the head of the patient, wherein the drive system at least comprises a driving device, a rotating device, and a connecting rod, wherein the driving device is arranged in at least a partial region of the second unit and is transmissibly connected to one end of the connecting rod, while an opposite end of the connecting rod extends to the first unit in a direction from the second unit to the first unit and is rotatably connected to the rotating device provided in the first unit to form the drive system, and the drive system serves to transmit a force generated by the driving device to the rotating device through the connecting rod, so that the rotating device receiving the force drives the first unit to move upward or downward with respect to the second unit.

5. The EEG cap of claim 4, wherein the rotating device comprises a damping shaft and a base, wherein the damping shaft connected to one end of the connecting rod is fixed to the base through at least one fixing point provided on the base, while a different part of the base is connected to the first unit, so that the damping shaft is configured to be driven by the force that is transmitted by the connecting rod and drive the base and further the first unit to move upward or downward with respect to the second unit.

6. The EEG cap of claim 4, wherein each constituent block further comprises a drive controlling device electrically connected to a detecting device, and the drive controlling device is further electrically connected to the driving device, so that a distance value measured by the detecting device is configured to be at least transmitted to the drive controlling device, or so that the drive controlling device is configured to at least transmit an electrical signal to the driving device, thereby changing operational parameters of the driving device.

7. The EEG cap of claim 4, wherein the connecting rod is installed in the at least partial region of the second unit, and has at least a portion of its rod body formed with threads while the rest of the rod body has a smooth surface.

8. The EEG cap of claim 7, wherein the connecting rod extends to a joint between the second unit and the first unit along a central axis passing through the first unit and the second unit and is rotatably connected to the rotating device located at the corresponding edge of the first unit.

9. The EEG cap of claim 8, wherein a threaded shaft of the driving device extending along the direction of the connecting rod and parallel to the connecting rod is configured to engage with the threaded portion of the connecting rod, so that when it is necessary to move the first unit upward or downward, the driving device is powered to drive a rotational shaft to rotate clockwise or anticlockwise and in turn drive the connecting rod to move forward and backward along the direction of the connecting rod by means of the threaded engagement.

10. The EEG cap of claim 9, wherein a base is integrated with or screw-fixed to a damping shaft, or screw-fixed to an edge of the first unit.

11. The EEG cap of claim 10, wherein the base is oriented such that the damping shaft is parallel to the edge of the first unit.

12. The EEG cap of claim 11, wherein the damping shaft has at least one part thereof integrated with or detachably screwed to a connecting end fixed to one end of the connecting rod.

13. The EEG cap of claim 12, wherein the connecting end is detachably fixed to the connecting rod using a combination of a screw rod and a threaded through hole, so that any damaged or broken first or second unit can be detached for replacement or repairment.

\* \* \* \* \*